(12) United States Patent
McKinnon et al.

(10) Patent No.: US 8,062,267 B2
(45) Date of Patent: Nov. 22, 2011

(54) VASCULAR ACCESS DEVICE INCLUDING A TEAR-RESISTANT SEPTUM

(75) Inventors: Austin Jason McKinnon, Herriman, UT (US); William G. Moulton, West Jordan, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 316 days.

(21) Appl. No.: 11/866,826

(22) Filed: Oct. 3, 2007

(65) Prior Publication Data

US 2008/0086099 A1  Apr. 10, 2008

Related U.S. Application Data

(60) Provisional application No. 60/828,359, filed on Oct. 5, 2006.

(51) Int. Cl.
*A61M 5/24* (2006.01)
*A61M 5/28* (2006.01)
*A61M 39/00* (2006.01)
*A61M 39/10* (2006.01)
*A61M 25/16* (2006.01)
*A61M 25/18* (2006.01)

(52) U.S. Cl. ........... 604/201; 604/533

(58) Field of Classification Search ........... 604/288.01–288.04, 86, 201–206, 604/533–534
See application file for complete search history.

(56) References Cited

U.S. PATENT DOCUMENTS

| | | | |
|---|---|---|---|
| 4,416,661 A * | 11/1983 | Norman et al. | 604/86 |
| 4,765,588 A | 8/1988 | Atkinson | |
| 5,085,645 A | 2/1992 | Purdy et al. | |
| 5,123,677 A * | 6/1992 | Kreczko et al. | 285/24 |
| 5,251,873 A | 10/1993 | Atkinson et al. | |
| 5,295,657 A | 3/1994 | Atkinson | |
| 5,295,658 A | 3/1994 | Atkinson et al. | |
| 5,342,316 A | 8/1994 | Wallace | |
| 5,354,275 A * | 10/1994 | Behnke et al. | 604/86 |
| 5,441,487 A | 8/1995 | Vedder | |
| 5,470,319 A | 11/1995 | Mayer | |
| 5,474,544 A | 12/1995 | Lynn | |
| 5,501,426 A | 3/1996 | Atkinson et al. | |
| 5,533,708 A | 7/1996 | Atkinson et al. | |
| 5,549,651 A | 8/1996 | Lynn | |
| 5,578,059 A * | 11/1996 | Patzer | 604/249 |
| RE35,841 E | 7/1998 | Frank et al. | |
| 5,873,862 A | 2/1999 | Lopez | |
| 5,928,204 A | 7/1999 | Lopez | |
| 5,957,898 A | 9/1999 | Jepson et al. | |
| 5,964,485 A * | 10/1999 | Hame et al. | 285/320 |
| 6,171,287 B1 | 1/2001 | Lynn et al. | |
| 6,261,282 B1 | 7/2001 | Jepson et al. | |
| 6,344,033 B1 | 2/2002 | Jepson et al. | |
| 6,595,964 B2 | 7/2003 | Finley et al. | |
| 6,651,956 B2 | 11/2003 | Miller | |
| 6,669,681 B2 | 12/2003 | Jepson et al. | |
| 6,716,396 B1 * | 4/2004 | Anderson et al. | 422/99 |
| 6,808,161 B1 | 10/2004 | Hishikawa | |

(Continued)

*Primary Examiner* — Nicholas Lucchesi
*Assistant Examiner* — Rebecca E Eisenberg
(74) *Attorney, Agent, or Firm* — Mony R. Ghose; Kirton & McConkie

(57) ABSTRACT

A vascular access device may include a body, a single-disk septum in communication with the body, and a rigid member supporting the septum. A method of manufacturing a vascular access device may include providing a body, providing a single-disk septum in communication with the body, and supporting the septum with a rigid member.

7 Claims, 9 Drawing Sheets

U.S. PATENT DOCUMENTS

| | | |
|---|---|---|
| 6,866,656 B2 | 3/2005 | Tingey et al. |
| 6,908,459 B2 | 6/2005 | Harding et al. |
| 2002/0032433 A1 | 3/2002 | Lopez |
| 2002/0133124 A1 | 9/2002 | Leinsing et al. |
| 2002/0138068 A1* | 9/2002 | Watson et al. ............. 604/891.1 |
| 2002/0193752 A1 | 12/2002 | Lynn |
| 2004/0006330 A1 | 1/2004 | Fangrow, Jr. |
| 2004/0068238 A1 | 4/2004 | Utterberg et al. |
| 2004/0068239 A1 | 4/2004 | Utterbberg et al. |
| 2004/0228208 A1 | 11/2004 | Papania et al. |
| 2005/0256500 A1 | 11/2005 | Fujii |

\* cited by examiner

VASCULAR ACCESS DEVICE INCLUDING A TEAR-RESISTANT SEPTUM

RELATED APPLICATIONS

This application claims the benefit of U.S. Provisional Application No. 60/828,359, filed Oct. 5, 2006, entitled VASCULAR ACCESS DEVICE INCLUDING A TEAR-RESISTANT SEPTUM, which is incorporated herein by reference.

BACKGROUND OF THE INVENTION

The present disclosure relates to infusion therapy with vascular access devices. Infusion therapy is one of the most common health care procedures. Hospitalized, home care, and other patients receive fluids, pharmaceuticals, and blood products via a vascular access device inserted into the vascular system. Infusion therapy may be used to treat an infection, provide anesthesia or analgesia, provide nutritional support, treat cancerous growths, maintain blood pressure and heart rhythm, or many other clinically significant uses.

Infusion therapy is facilitated by a vascular access device. The vascular access device may access a patient's peripheral or central vasculature. The vascular access device may be indwelling for short term (days), moderate term (weeks), or long term (months to years). The vascular access device may be used for continuous infusion therapy or for intermittent therapy.

A common vascular access device is a plastic catheter that is inserted into a patient's vein. The catheter length may vary from a few centimeters for peripheral access to many centimeters for central access. The catheter may be inserted transcutaneously or may be surgically implanted beneath the patient's skin. The catheter, or any other vascular access device attached thereto, may have a single lumen or multiple lumens for infusion of many fluids simultaneously.

Vascular access devices commonly include a Luer adapter, or other connector or adapter, to which other medical devices may be attached. For example, an IV (intravenous) administration set may be attached to a vascular access device to provide a fluid conduit for the continuous infusion of fluids and pharmaceuticals from an intravenous (IV) bag. A variety of medical devices may cooperate with vascular access devices to provide selective, temporary, or long-term access to the vascular system of a patient. A vascular access device may include a body having a lumen therethrough and a septum for selectively closing the lumen. The septum may be opened with a blunt cannula, a male Luer of a medical device, or other suitable medical device.

Vascular access devices provide many significant benefits to patients and medical practitioners. A vascular access device is most beneficial to patients when the septum forms a proper seal between the accessed vascular system and the outside or external environment. In an ideal vascular access device, the septum would continuously seal the patient's vascular system, which may include external vascular equipment intentionally coupled to the patient's internal vascular system by a medical practitioner, from the external environment.

As with most systems, one of the biggest challenges to the proper function of the vascular access device is when there is a change in the system, such as when different medical devices are connected or disconnected from the vascular access device. If the seal against the external environment is broken during the connection or disconnection of a medical device, there is the possibility of infection being introduced into the patient's vascular system. Additionally, if a pressure difference is created across the vascular access device, there becomes the possibility that blood will be drawn up the catheter system and possibly into the vascular access device or beyond. Alternatively, a pressure difference across the vascular access device may make it more difficult to couple other medical devices to the vascular access device.

As introduced above, vascular access devices are often coupled with a blunted cannula, such as the tip of a syringe, with a male Luer connector, or with other medical devices. These medical devices may be coupled to the vascular access devices by pressing a portion of the medical device into a slit or passage in the septum. Some medical devices are coupled to the vascular access device through a twisting motion by which the body or other portion of the medical device is coupled to the body of the vascular access device and by which a portion of the medical device is disposed in the slit or passage of the septum. Other methods of coupling the vascular access device to one or more medical devices may be used as well.

Regardless of the methods used to couple medical devices to the vascular access device, repeated transitions of the septum between open and closed configurations applies stress to the septum. In some experiences the septum has been seen to tear, either slightly or more significantly, at the edges of the slit that allows other devices to access the internal vascular system through the lumen of the body. In previous vascular access devices, two common tear patterns have been observed: radial tearing and circumferential tearing. Depending on the nature of the tear, the impacts of the tear may include a decrease in the quality of the seal formed by the septum or pieces or particles of the septum breaking free from the remainder of the septum. In any event, a septum that is modified from the manufacturer's intended and safety-tested design is not preferred for a number of reasons. The present disclosure is directed to vascular access devices, and methods of manufacturing vascular access devices, that include tear-resistant septum methods, systems, and devices.

BRIEF SUMMARY OF THE INVENTION

A vascular access device may include a body, a single-disk septum, and a rigid member. The body may define a lumen extending through the body. The single-disk septum may be in communication with the body, and the septum may at least substantially seal the lumen extending through the body. The rigid member may support and/or provide stability to the septum.

The rigid member may support the septum to prevent the septum from becoming unsealed and/or from opening in a direction away from the body. The septum may include a slit, and the septum may be a substantially flat disk having a duck-bill formed on an inferior portion of the slit of the septum. The body may include a top surface, and the septum may reside on the top surface of the body. The rigid member may be a cap securable to the body. The cap may open upon activation by an operator of the vascular access device. The cap may also include two arms secured to the body and biased towards a closed position. The rigid member may be a ring encircling the septum. The rigid member may be the body.

A method of manufacturing a vascular access device may include providing a body defining a passage extending therethrough, providing a single-disk septum, disposing at least a portion of the septum in communication with the body, at least substantially sealing the passage extending through the body with the septum, providing a rigid member in communication with the septum, and/or supporting the septum with the rigid member. The method may also include securing the rigid member to the body, coating the septum with an antimicrobial substance, hinging the rigid member to the body, discouraging the septum from unsealing, discouraging the septum from opening in a direction away from the body, and/or encircling the septum with the rigid member.

A vascular access device may include a body means, a sealing means, and/or a means for supporting the sealing means. The body means may be a body means for selectively coupling to a vascular system of a patient and to at least one additional medical device. The body means may have a passage extending therethrough. The sealing means may include a slit for selectively and at least substantially sealing the passage through the body. The means for supporting the sealing means may be in removable communication with the sealing means. The means for supporting the sealing means may encircle the sealing means.

These and other features and advantages of the present disclosure may be incorporated into vascular access devices and will become more fully apparent from the following description and appended claims, or may be learned by the practice and implementation of the present disclosure. As described above, the present disclosure does not require that all of the features described herein be incorporated into every embodiment nor is it required that certain features be used exclusive of other features. Vascular access devices within the scope of the present disclosure may include one or more combinations of the features described herein.

BRIEF DESCRIPTION OF THE SEVERAL VIEWS OF THE DRAWINGS

In order that the above-recited and other features and advantages of the disclosure may be readily understood, a more particular description is provide below with reference to the appended drawings. These drawings depict only exemplary embodiments of vascular access devices according to the present disclosure and are not therefore to be considered to limit the scope of the disclosure.

DETAILED DESCRIPTION OF THE INVENTION

It will be readily understood that the components of the present disclosure, as generally described and illustrated in the figures herein, could be arranged and designed in a wide variety of different configurations. Thus, the following more detailed description, as represented in the figures, is not intended to limit the scope of the disclosure, but is merely a representative of exemplary combinations of the components.

Figure 1:
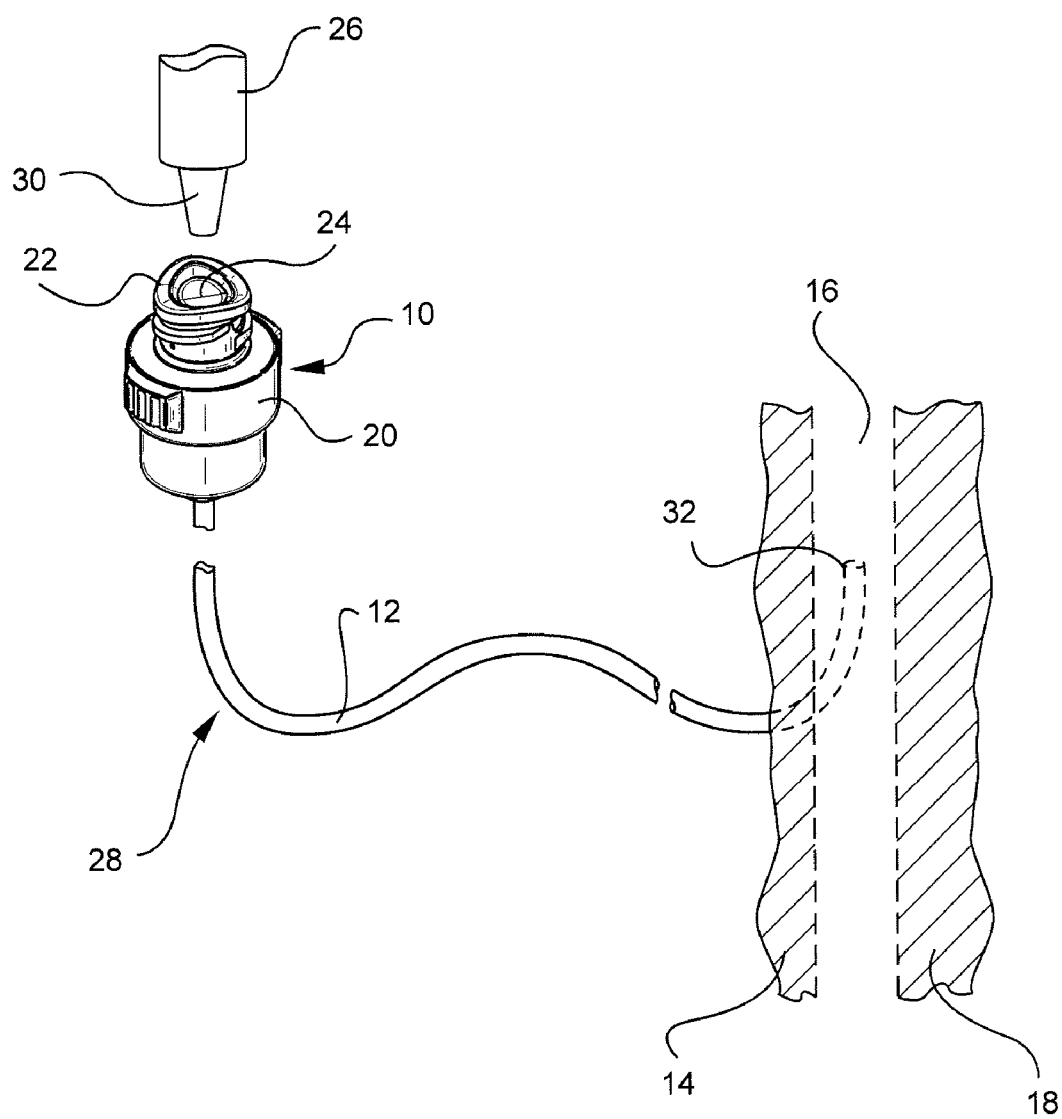
FIG. 1 is a perspective view of an extravascular system connected to the vascular system of a patient.

Referring now to FIG. 1, a vascular access device 10 is used to introduce a substance via a catheter 12 across the skin 14 and into a blood vessel 16 of a patient 18. The vascular access device 10 includes a body 20 with a lumen and a septum 22 placed within the lumen. The vascular access device 10, including the body 20 and the septum 22, will be more thoroughly described with reference to the remaining figures where particular features are better illustrated. As shown in FIG. 1, the septum 22 has a slit 24 through which a separate extravascular device 26, such as a syringe, may introduce a substance into the vascular access device 10. A syringe is one exemplary separate device 26. Other suitable extravascular devices may include additional vascular access devices, IV administration sets, or other common or yet to be developed medical devices.

The device 10 and all structures used in combination therewith may form a larger extravascular system 28. As part of operating the extravascular system 28, a tip 30 of the separate device 26 may be inserted into the vascular access device 10 through the slit 24 of the septum 22. The tip 30 penetrates the device 10 separating at least portions of the two opposing slit surfaces of the septum 22. The septum 22 and the slit 24 may be configured to seal, or at least substantially seal, around the tip 30 as it is inserted into the vascular access device 10. Accordingly, the surfaces near the slit ends may not be separated until the tip 30 is sufficiently inserted into vascular access device 10. The tip 30 serves to open the slit 24 to allow fluid to pass through the device 10, into the catheter 12, and out the end 32 of the catheter when the device is in use.

Figure 2:
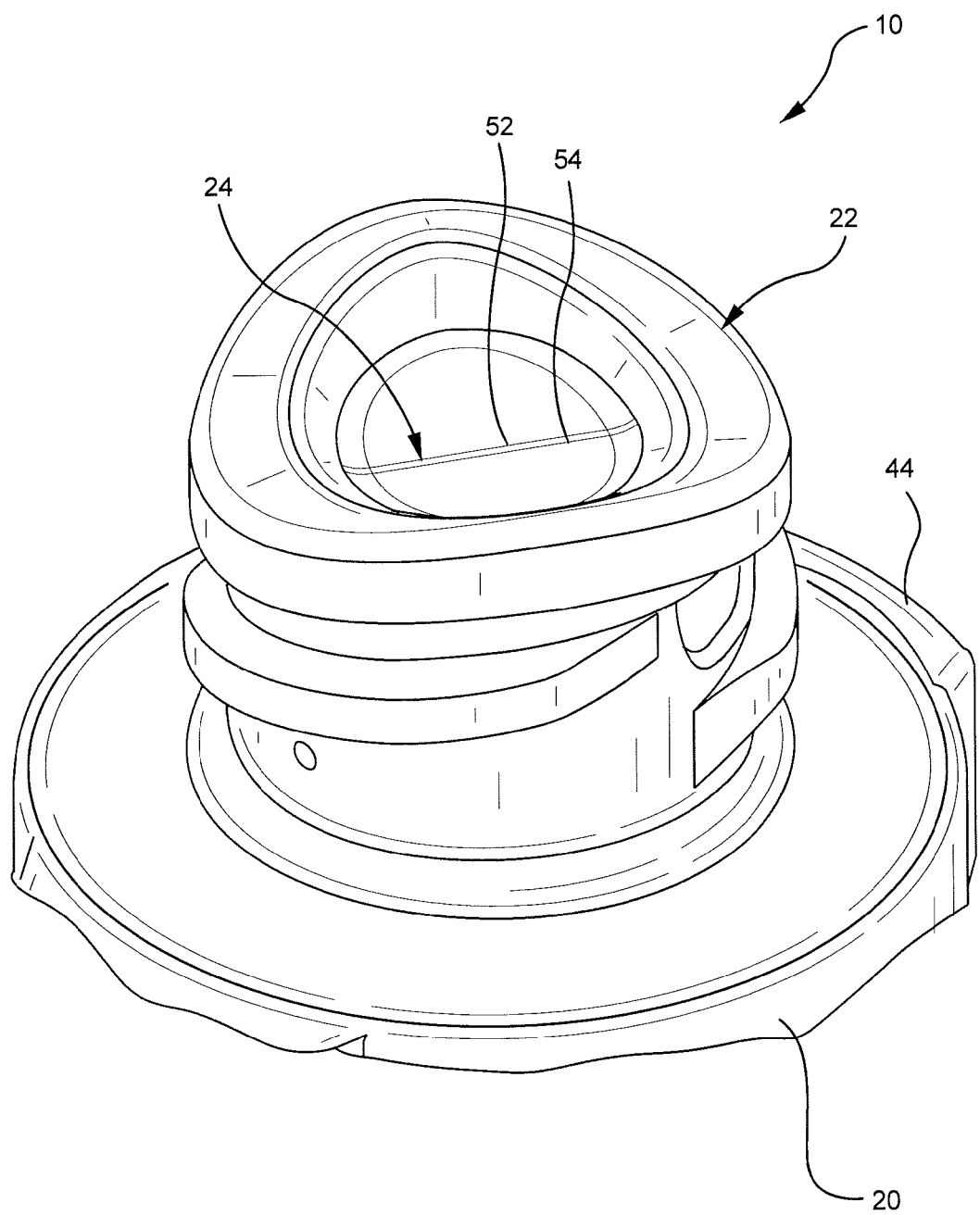
FIG. 2 is a top view of a vascular access device.
Figure 3:
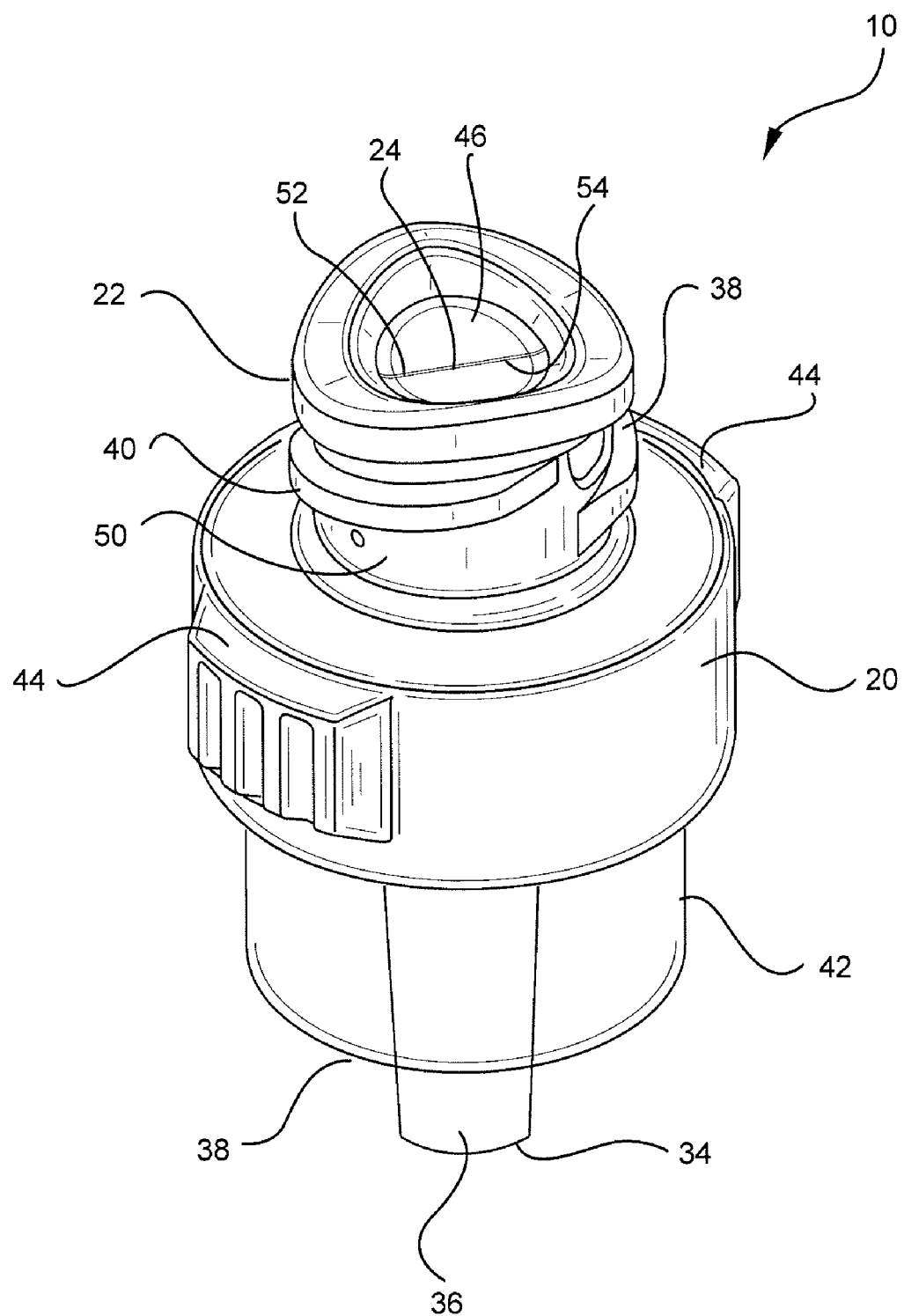
FIG. 3 is a perspective side view of a vascular access device.

The features of an example of a vascular access device 10 are illustrated in FIGS. 2 and 3. As illustrated in these figures, the septum 22 includes a portion that extends beyond the body 20 but is otherwise disposed substantially within the body 20. The body 20 may include a cannula 34 for coupling with a catheter or other medical device. The cannula 34, along with other components of the body 20, may cooperate to form a lumen 36 through the body 20. The body 20 may also include connection regions 38, such as female Luer connector 40 or male Luer connector 42, to enable the vascular access device to be selectively coupled to other medical devices. Additionally, the body 20 may include grips 44, which may be ridges or other structures on the surface of the body 20, to facilitate the manipulation of the vascular access device 10. The body 20 may include other features or structures common to vascular access devices.

Figure 4:
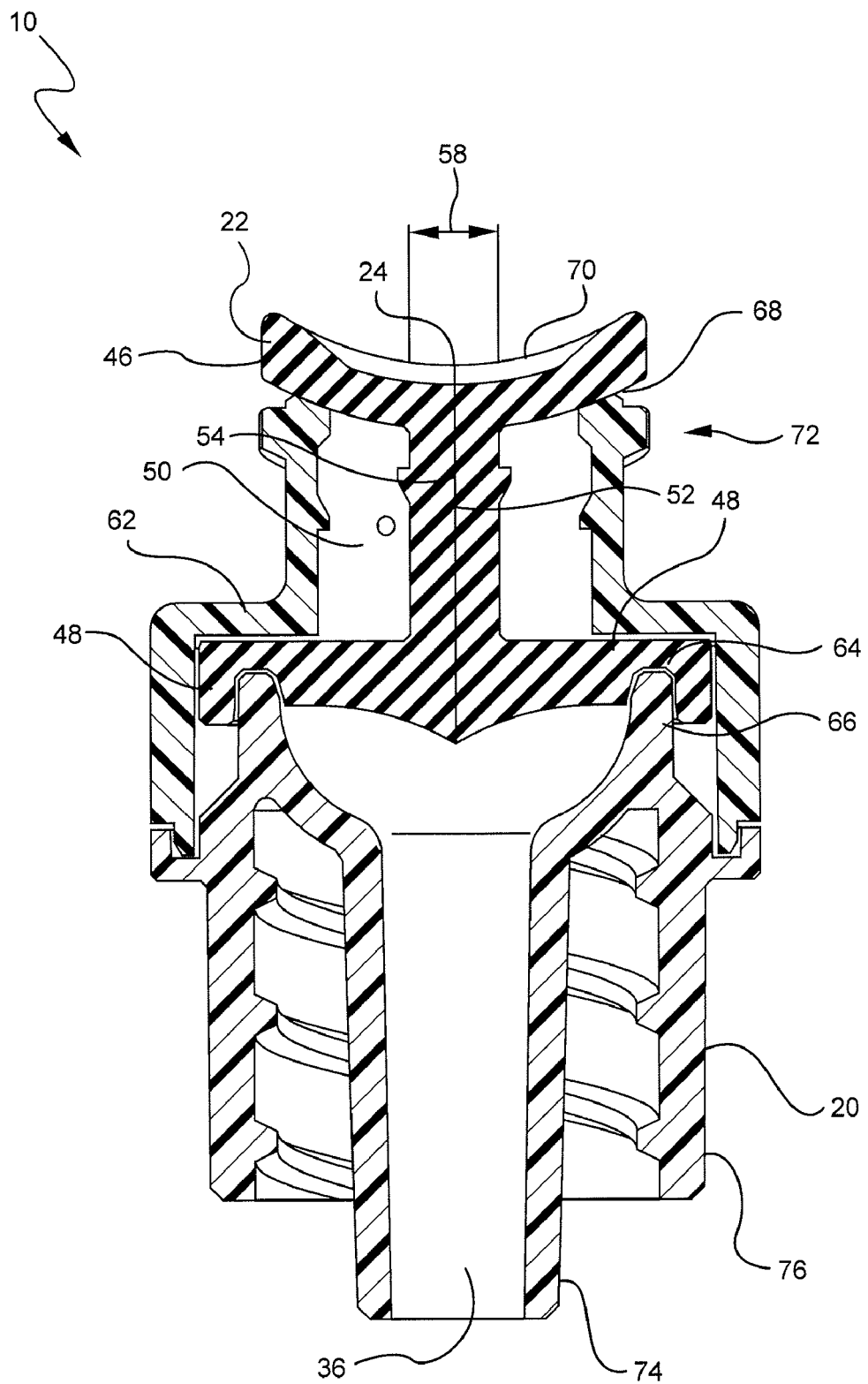
FIG. 4 is a cross section view of a vascular access device.

With continuing reference to FIGS. 2-4, the septum 22 is substantially disposed within the body 20 of the vascular access device 10. More specifically, the septum 22 includes a top disk 46, a bottom disk 48, and a throat region 50 extending between the top disk 46 and the bottom disk 48. The throat section 50 and bottom disk 46 are more clearly visible in the cross section view presented in FIGS. 4 and 5. As used herein, the top disk 46 may also be referred to as a saddle 46 and the bottom disk 48 may be referred to as an anchor 48. With more particular reference to FIG. 2, the septum 22 is shown to include a slit 24 having opposing slit surfaces 52, 54. As described above, the opposing slit surfaces 52, 54 of the slit 24 are moved apart to open the slit when the tip 30 of a medical device is inserted into a vascular access device 10.

Figure 5:
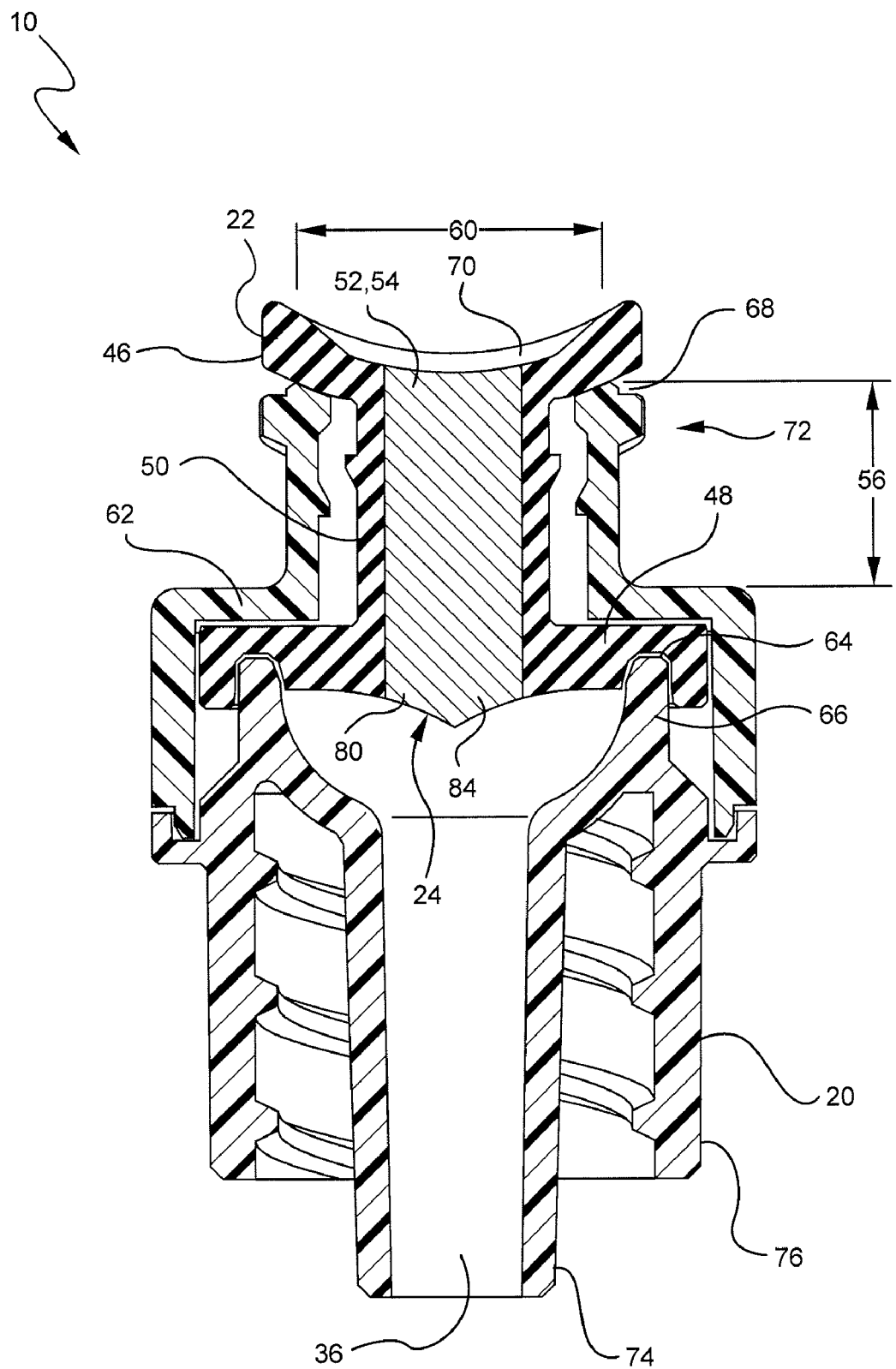
FIG. 5 is a cross section view of a vascular access device with the cross section being 90 degrees offset from the cross section of FIG. 4.

Referring now to FIGS. 4 and 5, cross sectional views of a vascular access device 10 are shown to better illustrate particular aspects of an exemplary septum 22. As illustrated, FIGS. 4 and 5 are cross sections of the same vascular access device with the cross sections being taken along orthogonal lines of cross section. FIG. 4 illustrates a vascular access device 10 showing the throat region 50 spanning between the saddle 46 and the anchor disk 48. The throat region 50 may have any suitable length 56 between the saddle 46 and the anchor 48, which length 56 may vary to accommodate the configuration of the body 20. As one example, the length 56 may be selected to position the anchor disk 48 within the body 20 and the saddle 46 outside the body, as illustrated.

The throat region 50 also has a thickness 58, shown in FIG. 4, and a width 60, shown in FIG. 5. The width 60 and thickness 58 of the throat region 50 may be selected to meet the needs of the medical practitioner and the vascular access device 10 in which the septum 22 is being incorporated. The width 60 may be selected to provide sufficient room for a slit 24 sufficiently wide to accommodate the desired tips 30 of the cooperating medical devices 26. The thickness 58 of the throat region 50 may be selected to provide sufficient strength to the throat region while still providing sufficient elasticity and/or flexibility to allow the slit surfaces 52, 54 to separate as the tips 30 are inserted into the vascular access device 10.

The bottom disk 48, or anchor disk, may be configured to have a size, such as a diameter, that is selected to fit within the body 20 and to be retained in the body by a shoulder region 62. Additionally or alternatively, the bottom disk 48 may be anchored within the body 20 through other means, such as through adhesives or fasteners. As illustrated in FIGS. 4 and 5, the bottom disk 48 may include one or more grooves or slots 64 that may be adapted to cooperate with portions of the body 20 to further anchor the septum 22 in place. The bottom disk 48 and one or more portions of the body 20 may be configured to anchor the septum 22 rotationally within the body, longitudinally within the body, and/or laterally within the body. As one example, fingers 66 of the body 20 may be adapted to fit in the grooves 64 to prevent lateral movement and/or rotational movement of the septum 22. Additionally or alternatively, the fingers 66 may be sized to press the bottom disk 48 into the shoulder region 62 so that the top surface of the bottom disk is in contact with the body 20. As one example, the fingers 66 may cause the bottom disk 48 and the body 20 to form a seal. In addition to the features described, the bottom disk 48 may include additional features or elements customary for vascular access devices.

FIGS. 4 and 5 illustrate that the top disk 46 may be configured to be disposed outside of the body 20. As illustrated the bottom surface of the top disk 46 rests on the upper end 68 of the body 20. FIG. 4 further illustrates that the top disk 46 may be configured to provide a well 70 or indentation. The well 70 may assist in guiding the tip 30 of the cooperating medical device 26 into the slit 24 of the vascular access device 10. As seen in FIGS. 4 and 5, the well 70, in some implementations, may cause the top disk 46 to resemble a saddle. The well 70, when present, may be formed by thinning a portion of the top disk 46 and/or by applying upward pressure to the outside edge of the top disk 46. As one example, the septum 22 may be configured with a throat region 50 that is minimally shorter than the distance between the shoulder region 62 of the body 20 and the upper end 68 of the body. Accordingly, the septum material of the throat region 50 and the top disk 46 may be slightly stretched by this difference causing the top disk to flex forming the well 70. The well 70 may be formed in other suitable manners.

As discussed above and as illustrated in FIG. 4, the top disk 46 contacts the upper end 68 of the body 20. The interface between the top disk 46 and the upper end 68 of the body 20 may form an additional seal, which may be similar to the seal between the bottom disk 48 and the body 20. Additionally or alternatively, an adhesive may be used to bond the top disk 46 to the upper end 68 of the body. Moreover, structural features, such as grooves, may be incorporated into the bottom surface of the top disk 46 to cooperate with the body 20 to form a seal.

The seals formed by the top disk 46 and/or the bottom disk 48 and the body 20 are adapted to seal, or at least substantially seal the lumen 36 through the body 20. Moreover, when the slit surfaces 52, 54 are together (i.e., not separated by a tip 30 and not otherwise separated by tears, cracks, or other modifications to the septum), the septum 22 seals, or at least substantially seals the passage through the lumen of the body 20.

For purposes of description, the upper end 68 of the body 20 and the portions adjacent thereto may be referred to as a first body end region 72 whereas the lower end 74 of the body 20 and the portions adjacent thereto may be referred to as the second body end region 76. The use of the terms first and second to denominate the end regions, or other elements described herein, is not meant to imply any order between the two end regions but merely to distinguish between the two. While the terms top and bottom are also used herein to designate and distinguish features, components, or parts of the vascular access device, it should be understood that the orientation of the vascular access device may change during use of the device; accordingly, the terms top and bottom are not intended to be limiting with respect to orientation during use of the device but are referencing relative locations in the figure being discussed.

The body 20 and the septum 22 may be constructed of a variety of suitable materials. Commonly, the body 20 of the vascular access device 10 will be made of a plastic, and preferably a plastic material that facilitates molding the body. As illustrated in FIGS. 4 and 5, the body 20 is formed from two pieces that are molded or adhered together to form the body once the septum 22 is in place. Other methods and materials may be used for manufacturing the body 20, some of which may be currently practiced and some of which may be developed in the future.

Similarly, the septum 22 may be made of a variety of suitable materials and through a variety of suitable manufacturing methods. For example, the septum may be formed from liquid silicone rubber through suitable molding procedures, such as insert molding, injection molding, other molding techniques, or a combination of molding techniques. The septum 22 may also be formed of any dimension capable of providing a slit 24 that, alone or in combination with other features, resists tearing when accessed by a separate vascular access device 26.

Figure 6:
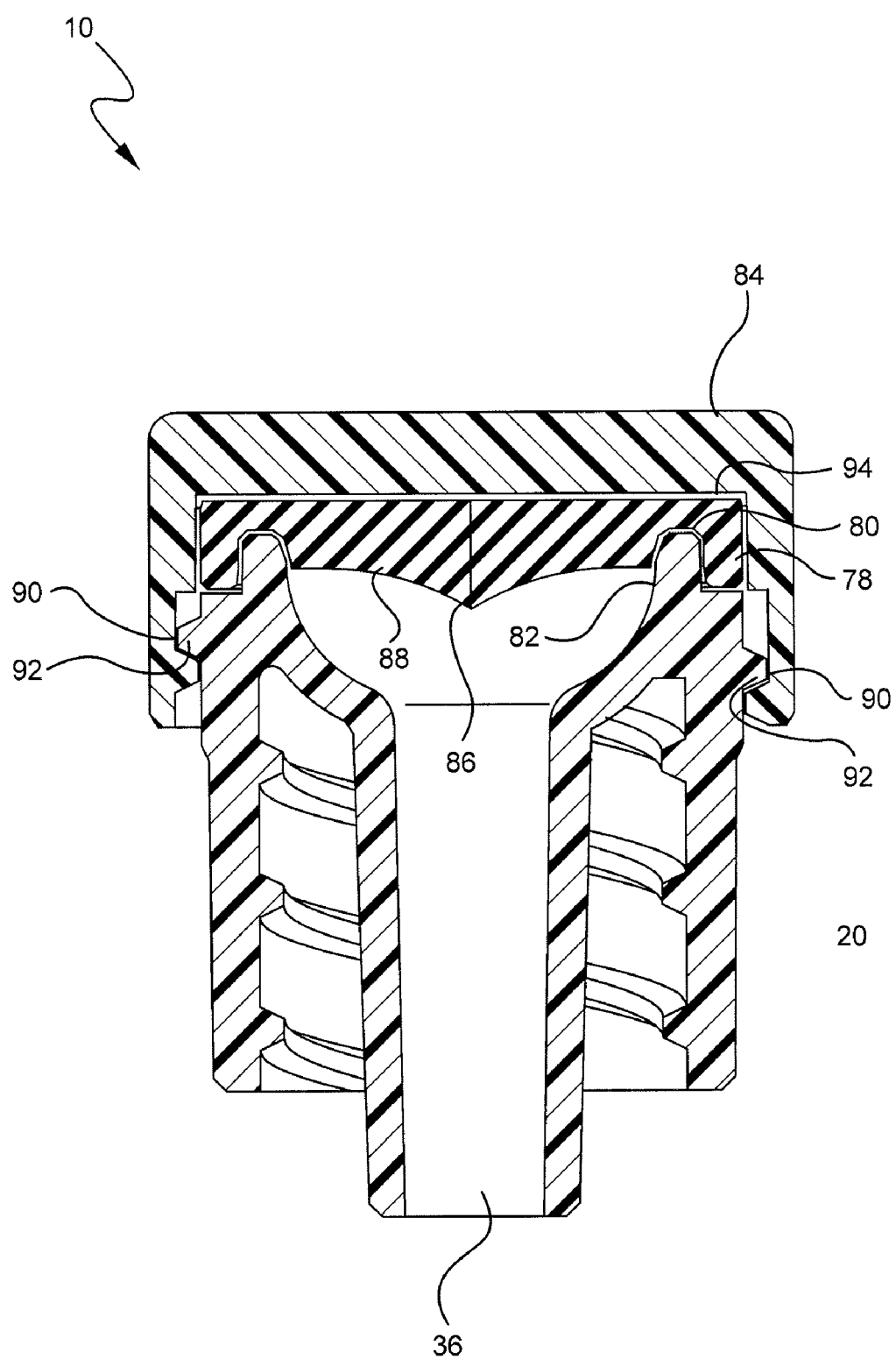
FIG. 6 is a cross section view of a rigid member secured to a vascular access device.

Referring now to FIG. 6, an example of a septum having dimensions or structure that is different than the septum 22 described with reference to FIGS. 1 through 5 is shown and described. A single-disk septum 78, or a single-layer septum 78, may be secured to the body 20 of a vascular access device 10 in order to facilitate a wider slit 24 that will resist tearing when accessed by a separate vascular access device 26. The single-disk septum 78 is in communication with the body 20 and substantially seals the lumen 36 extending through the body 20. The single-disk septum 78 is secured to the top surface 80 of the body 20 using an adhesive, mechanical attachment, or other similar means of attachment. The single-disk septum 78 may also be secured at any point along the inner surface 82 of the body 20.

The septum 78 includes the slit 24 and is a substantially flat disk having a duck-bill 86 formed on the inferior portion or surface 88 of the slit 24 of the septum 78. The duck-bill 86 serves as additional material providing additional structural support to the septum 78 intended to prevent or discourage the septum 78 from opening in a direction away from the general direction of the body 20. The duck-bill 86 combined with the rigid member 84 may be used to strengthen the septum 78 against back pressure flowing through the lumen 36 in a direction through the slit 24 towards the external environment in which the device 10 is placed.

A rigid member 84 supports the septum 78 to prevent the septum 78 from becoming unsealed, and thus allowing the environment within the lumen 36 to communicate with the external environment in which the device 10 is placed. The rigid member 84 also supports the septum 78 to prevent the septum from opening in a direction away from the general direction of the body 20.

The rigid member 84 is a cap securable to the body 20. The rigid member 84 may alternatively or additionally take any other form, dimension, or material capable of providing the needed protection and support to the septum 78. The cap or rigid member 84 is securable to the body 20 by means of female threads 90 formed within the rigid member 84 that correspond with male threads 92 on the external surface of the body 20. Any other mechanical or other means of securing the cap or rigid member 84 may be employed to secure the rigid member 84 to the body.

The septum 78, or any septum described herein, may also include a coating of antimicrobial substance 94 on any of its surfaces. The coating 94, as shown in FIG. 6, may exist between the top surface of the septum 78 and the bottom surface of the rigid member 84. The antimicrobial substance 94 may be applied to the top surface of the septum 78, or to any other septum described herein, when the rigid member 84 is placed in contact with any surface of the septum 78.

A single-layer or single-disk septum 78 eliminates the need to provide a throat region 50 and a bottom disk 48. Traditionally, the bottom disk 48 and throat 50 provide additional support necessary to ensure that the septum 22 remains closed in the presence of active use and back pressure within the lumen 36. However, by providing the additionally structural support and stability of a rigid member as described in the various embodiments herein, a single-layer or single-disk septum or other septum with less substantial structure may be adequately supported against back pressure and other influences exerted upon the septum in order to function properly. Thus, various alternate embodiments illustrating different examples of septums and rigid members may be provided and will be described herein.

Figure 7:
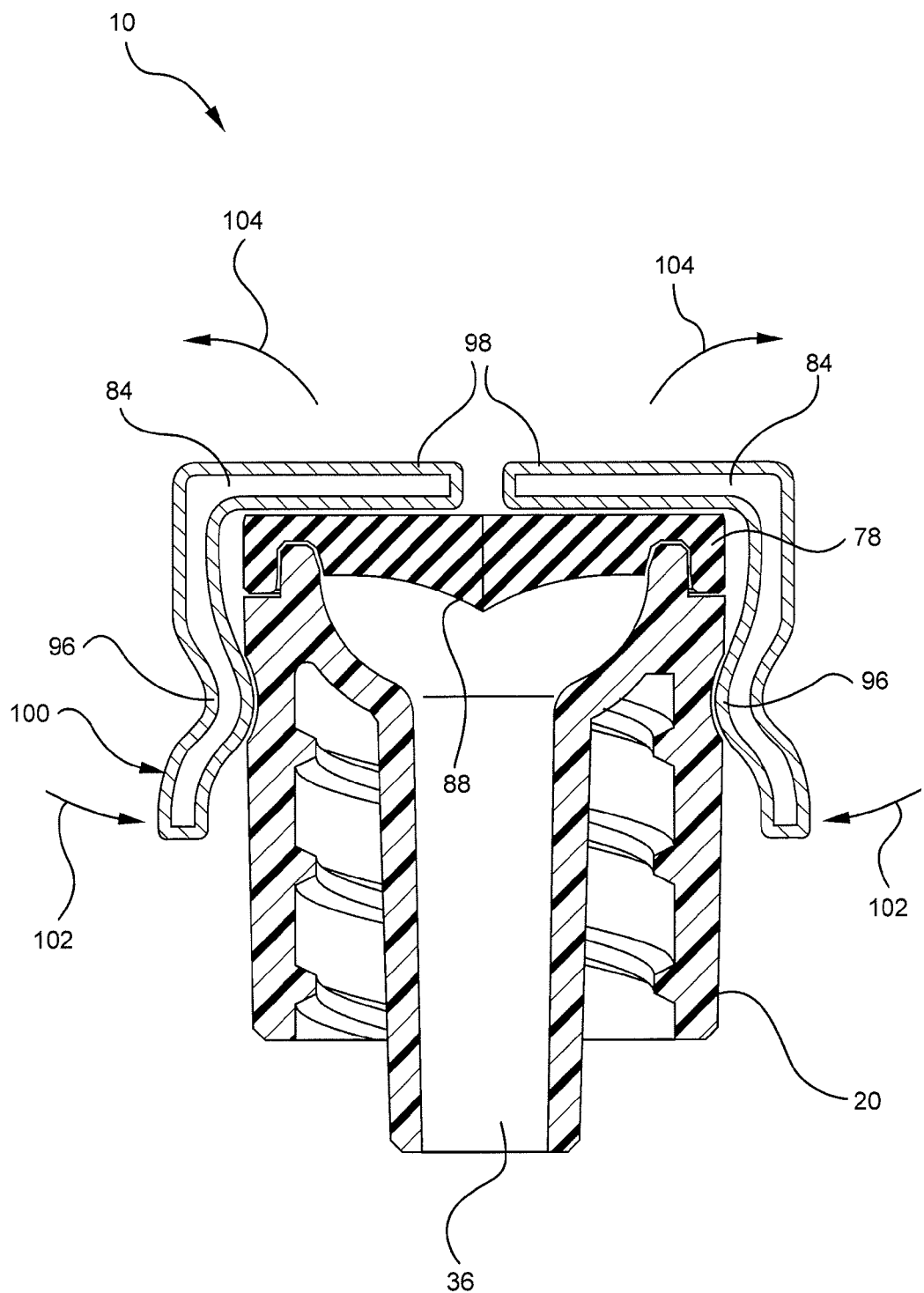
FIG. 7 is a cross section view of multiple rigid members secured to a vascular access device.

Referring now to FIG. 7, multiple or rigid members 84 may be secured to the body 20 of a vascular access device 10 to form a cap which may open upon activation by an operator of the device 10. The multiple rigid members 84 are two arms secured to the body 20 and biased towards a closed position by means of a spring 96 securing each of the two rigid members 84 individually to the body 20. Any other spring or resilient means or structure may be provided in place of the springs 96 in order to bias the rigid members 84 towards a closed position.

With the rigid members 84 in closed position, a top portion 98 of the rigid members 84 strengthens and protects a septum 78 from opening in a direction away from the body 20 when back pressure through a lumen 36 of the body 20 creates force against an inferior surface 88 of the septum 78. The top portions 98 may be removed away from the top surface of the septum 78 to expose the septum 78 for access by a separate access device 26. Thus, the cap formed by the rigid members 84 may open upon activation by an operator of the device 10. In a similar manner, the cap or rigid member 84 described with reference to FIG. 6 may be removed or opened from the body 20 of the device 10 upon activation and use by an operator of the device 10.

To open or activate the rigid members 84 of the device 10 described with reference to FIG. 7, an operator may exert force upon the lower arms 100 of the rigid members 84 in a direction 102 towards the body 20. Since the lower portions 100 are below the hinge of the spring 96, as the lower portions 100 travel in a direction 102, the rigid members 84 hinge upon the pivot point of the springs 96, causing the top portion 98 of the rigid members 84 to travel in a direction 104 away from the body 20 and in a direction that is opposite to the direction 102.

With the rigid members 84 activated, the user may then access the septum 78 with a separate access device 26. After the septum 78 is accessed by a separate access device 26, a user may release the lower portions 100 of the rigid members 84 in order to permit the rigid members 84 to return to their original position, biased towards closed, and supporting the septum 78 against back pressure and other forces that may build within the lumen 36 or other surrounding environments.

Figure 8:
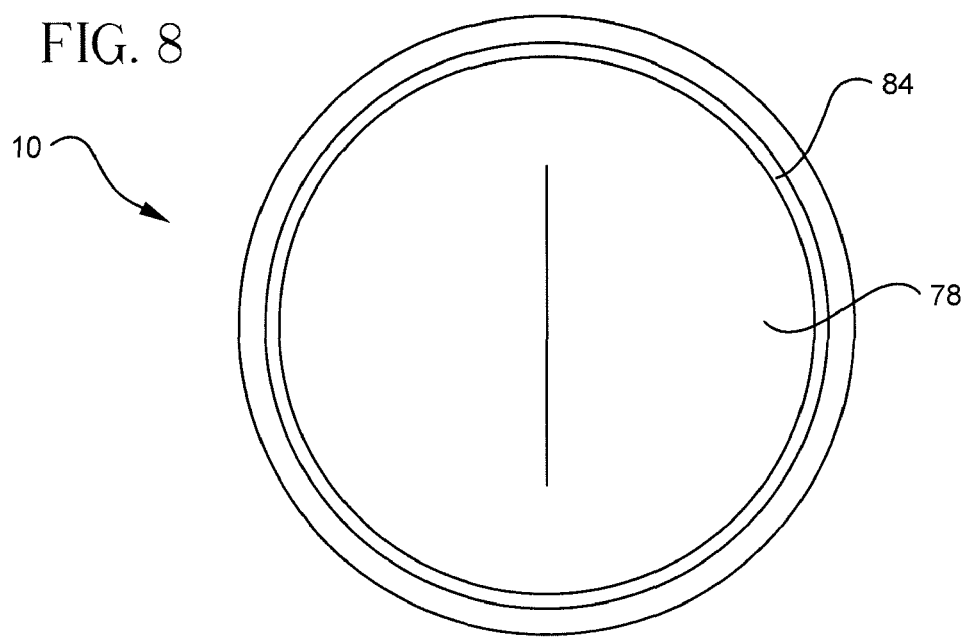
FIG. 8 is a top view of a rigid member and a septum of a vascular access device.

Referring now to FIG. 8, a top view of a rigid member 84 supporting a septum 78 of a vascular access device 10 is shown. The rigid member 84 is a ring encircling the septum 78. The rigid member 84 may include a material capable of providing additional support to the septum 78. For example, the rigid member may be thermal plastic molded around the septum 78, for example, using a two-shot molding process. The rigid member or ring 84 may also be bonded to the septum 78 and/or to the body 20 (see FIG. 9 below) using adhesive, ultrasonic bonding, or any other mechanical or other securing or attaching means. Additionally or alternatively, the rigid member 84 may be integrated directly into, or may be, the material of the body 20. For example, as described with reference to FIG. 6, the septum 78 may be placed within and against the interior surface 82 of the body 20 to use the body 20 as an additional rigid member supporting the septum 78.

Figure 9:
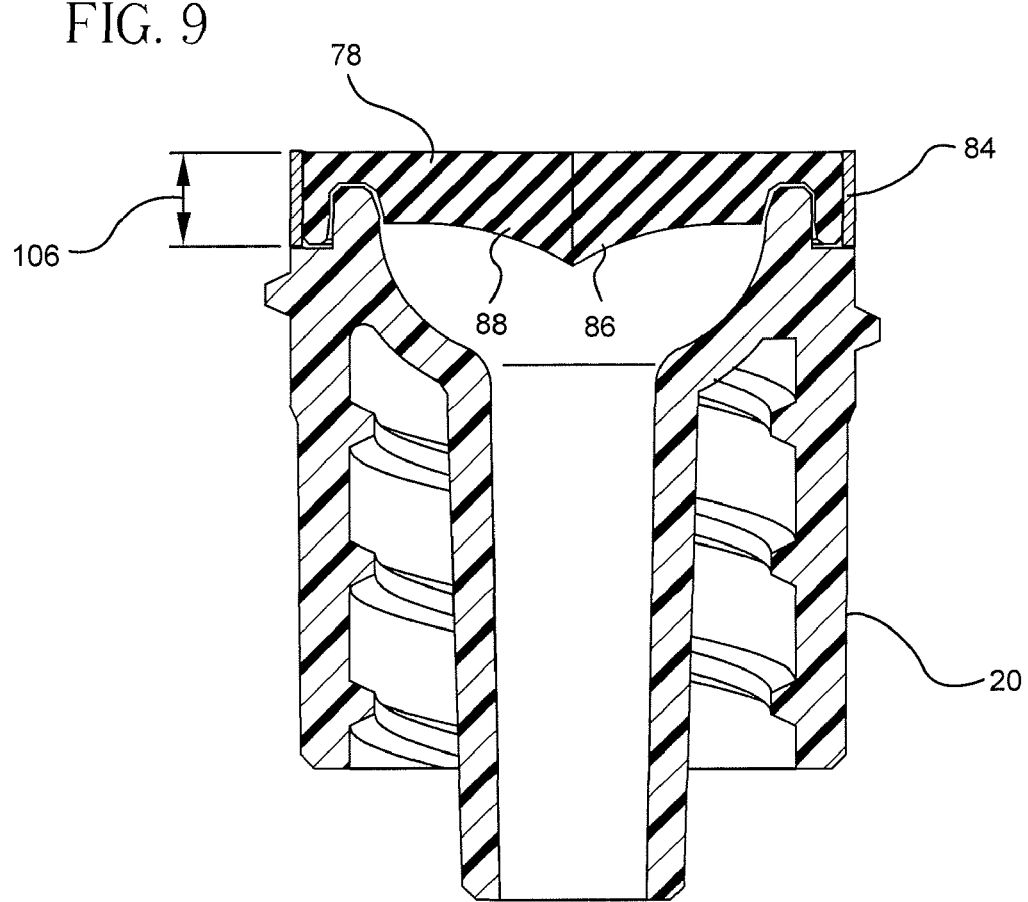
FIG. 9 is a side view of the rigid member of FIG. 8 secured to the body of a vascular access device.

Referring now to FIG. 9, a side view of the vascular access device 10 of FIG. 8 is shown. The rigid member 84 secures the outer surface of the septum 78. The septum 78 includes a thickness 106 that is generally greater than the thickness of the top disk 46 of the septum 22 described with reference to FIGS. 2 through 5. A septum 78 having a greater thickness 106 will provide additional support and stability which, when combined with the support and stability of the rigid member 84, will prevent or discourage the septum 78 from opening in a direction away from the general direction of the body 20 of the device 10.

Figure 10:
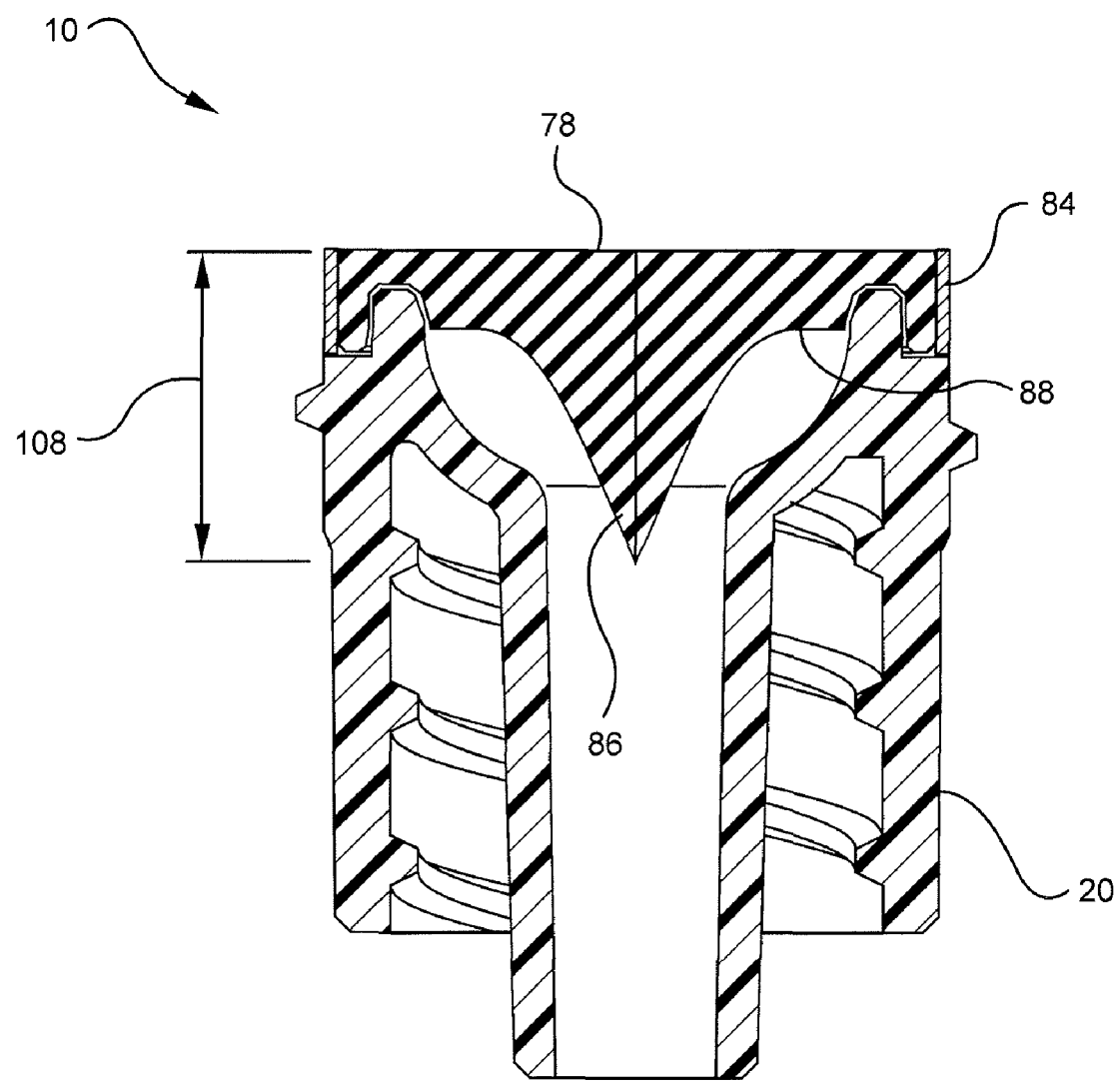
FIG. 10 is a side view of a vascular access device having an elongated septum.

Further, additional structure may be added to the septum 78 to provide additional support and stability. For example, a duck-bill 86 may be added to the inferior surface 88 of the septum 78 in order to provide additional support and/or stability. Further, as shown for example, in FIG. 10, the dimensions of the duck-bill 86 may be increased to provide a longer duck-bill 86 in order to provide further strength and/or stability to the septum 78. Thus, the overall width or thickness 108 may be increased as needed to provide the necessary support for the septum 78. Any other dimensions, materials, and/or orientations may be provided to ensure that the material of the septum 78 is adequately strong to resist back pressure or other environmental forces exerted upon the septum 78.

It is believed that the disclosure set forth above encompasses multiple distinct inventions with independent utility. While each of these inventions has been disclosed in its preferred form, the specific embodiments thereof as disclosed and illustrated herein are not to be considered in a limiting sense as numerous variations are possible. The subject matter of the inventions includes all novel and non-obvious combinations and subcombinations of the various elements, features, functions and/or properties disclosed herein. Where the disclosure, the presently filed claims, or subsequently filed claims recite "a" or "a first" element or the equivalent thereof, it should be within the scope of the present inventions that such disclosure or claims may be understood to include incorporation of one or more such elements, neither requiring nor excluding two or more such elements.

Applicants submit claims herewith and reserve the right to submit claims directed to certain combinations and subcombinations that are directed to one of the disclosed inventions and are believed to be novel and non-obvious. Inventions embodied in other combinations and subcombinations of features, functions, elements and/or properties may be claimed through amendment of those claims or presentation of new claims in that or a related application. Such amended or new claims, whether they are directed to a different invention or directed to the same invention, whether different, broader, narrower or equal in scope to the original claims, are also regarded as included within the subject matter of the inventions of the present disclosure.

The invention claimed is:

1. A vascular access device, comprising:
   a body having a top, a bottom, a lumen extending between the top and the bottom, and a top lumen opening defining an area;
   a septum coupled to the top of the body, the septum consisting of a disk having a substantially flat top surface and a slit, the septum spanning the top lumen opening, and a portion of the septum being directly above the area of the top lumen opening; and
   a rigid member disposed on the top of the body, the rigid member having a plurality of arms, each arm being secured to the body at a pivot point and coupled to a spring, each arm having a top portion above the pivot point and a lower portion below the pivot point, the spring biasing the upper portion of each arm toward the top surface of the septum such that the upper portion of each arm covers a substantial portion of the portion of the septum directly above the area of the top lumen opening.

2. The vascular access device of claim 1, wherein when a force is exerted on the lower portion of each arm in the direction of the body, the top portion of each arm moves in a direction away from the top portion of the septum.

3. The vascular access device of claim 2, wherein when the top portion of each arm moves in a direction away from the top portion of the septum the rigid member is in an open position in which the septum is accessible by a separate access device.

4. The vascular access device of claim 1, wherein when a force is exerted on the lower portion of each arm in the direction of the body, the top portion of each arm moves in a direction away from the top portion of the septum.

5. The vascular access device of claim 1, wherein the plurality of arms comprises two arms.

6. The vascular access device of claim 1, wherein the spring biases the arms to a closed position in which the upper portion of each arm is in contact with the top surface of the septum.

7. The vascular access device of claim 1, wherein the septum has a diameter and the slit of the septum has a length greater than one half the length of the septum diameter.

* * * * *